United States Patent
Laster et al.

(10) Patent No.: US 10,188,601 B2
(45) Date of Patent: Jan. 29, 2019

(54) CONTINUOUS LONG-TERM CONTROLLED RELEASE OF TELOMERASE INHIBITORS

(71) Applicant: Brenda Laster, Meitar (IL)

(72) Inventors: Brenda Laster, Meitar (IL); Josef Kost, Omer (IL)

(73) Assignee: Brenda Laster, Meitar (IL)

( * ) Notice: Subject to any disclaimer, the term of this patent is extended or adjusted under 35 U.S.C. 154(b) by 0 days.

(21) Appl. No.: 15/023,884

(22) PCT Filed: Sep. 21, 2014

(86) PCT No.: PCT/IL2014/050840
§ 371 (c)(1),
(2) Date: Mar. 22, 2016

(87) PCT Pub. No.: WO2015/040622
PCT Pub. Date: Mar. 26, 2015

(65) Prior Publication Data
US 2016/0228356 A1 Aug. 11, 2016

Related U.S. Application Data

(60) Provisional application No. 61/880,934, filed on Sep. 22, 2013.

(51) Int. Cl.
A61K 9/00 (2006.01)
A61K 31/555 (2006.01)
A61K 31/409 (2006.01)

(52) U.S. Cl.
CPC .......... *A61K 9/0024* (2013.01); *A61K 31/409* (2013.01); *A61K 31/555* (2013.01)

(58) Field of Classification Search
CPC ........................... A61K 31/409; A61K 31/555
See application file for complete search history.

(56) References Cited

U.S. PATENT DOCUMENTS

| 5,366,734 | A | | 11/1994 | Hutchinson | |
|---|---|---|---|---|---|
| 5,456,917 | A | * | 10/1995 | Wise | A61K 9/1647 424/422 |
| 6,087,493 | A | * | 7/2000 | Wheelhouse | C07D 487/22 435/6.12 |
| 6,206,920 | B1 | | 3/2001 | Eliaz et al. | |
| 2005/0112058 | A1 | * | 5/2005 | Laster | A61K 31/409 424/1.11 |
| 2008/0009473 | A1 | * | 1/2008 | Williams | C07D 487/22 514/185 |
| 2009/0304803 | A1 | * | 12/2009 | Hasan | A61K 41/0071 424/497 |

FOREIGN PATENT DOCUMENTS

| WO | 199833503 | A1 | | 8/1998 |
|---|---|---|---|---|
| WO | 2003063757 | A2 | | 8/2003 |
| WO | 2006133271 | A2 | | 12/2006 |
| WO | 2011/071970 | | * | 6/2011 |
| WO | 2011071970 | A2 | | 6/2011 |

OTHER PUBLICATIONS

Papanikolaou V. et al.," hTERT regulation by NF-κB and c-myc in irradiated HER2-positive breast cancer cells, International Journal of Radiation Biology", pp. 609-621, vol. 87, No. 6, (Jun. 2011).

* cited by examiner

*Primary Examiner* — Nicole P Babson
(74) *Attorney, Agent, or Firm* — Browdy and Neimark, PLLC

(57) ABSTRACT

Disclosed herein telomerase inhibitors and controlled-release formulations thereof, the use of telomerase-inhibiting porphyrins, especially metalloporphyrins, in the controlled-release intratumoral implants for the treatment of cancer. Provided herein also specific compositions of metalloporphyrins and poly-(lactic-co-glycolic)-acid copolymers, in various implantable forms, and methods of treatment cancer by administering the implants of the invention, alongside possible co-treatment with brachytherapy radioactive seeds to precipitate Auger effect of the metal atoms contained in the metalloporphyrins.

11 Claims, 10 Drawing Sheets

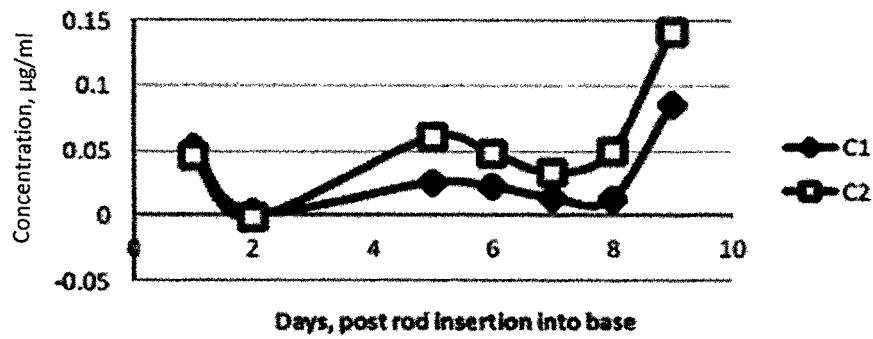
Figure 12
12a
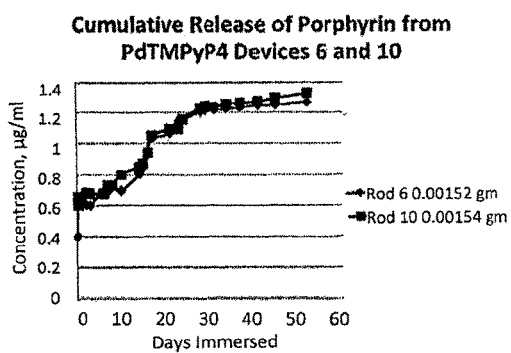
12b
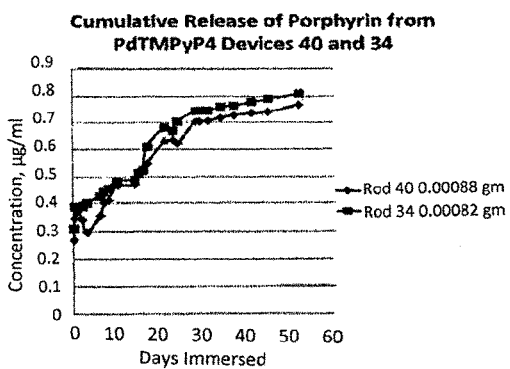
12c
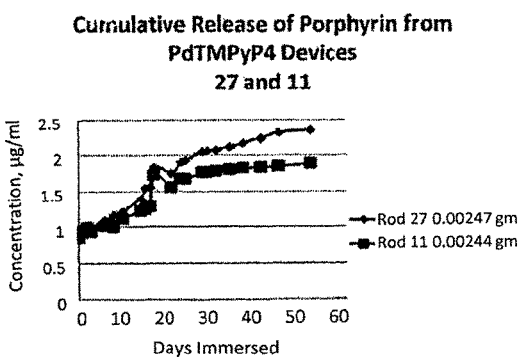
12d
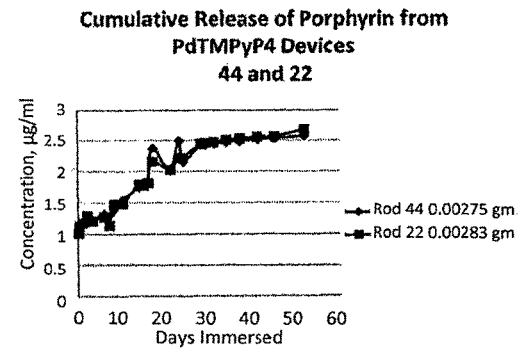

CONTINUOUS LONG-TERM CONTROLLED RELEASE OF TELOMERASE INHIBITORS

FIELD OF THE INVENTION

The present invention relates to the field of the treatment of cancer with telomerase-inhibiting drugs by means of an intratumoral drug delivery system that releases the drugs at a controlled rate, over a prolonged period of time, providing an extended release drug profile.

BACKGROUND OF THE INVENTION

The presence of the telomerase enzyme in the majority of cancers and its conferral of unrestricted proliferation to cancer cells presents a major dilemma in the treatment of cancer. Both radiation therapy and chemotherapy cause an increase in telomerase activity (TA) in cells comprising the tumor. When activated, the enzyme prevents the shortening of the telomeric ends of DNA and protects the chromosomal ends of DNA from deteriorating or combining with other chromosomes, by adding the TTAGGG sequences to the ends of chromosome's telomeres. Shortening of the telomeres causes the cancer cells to undergo various death modes or to become sensitive to various treatments and increases the probability of successful cancer therapy.

It may thus be appreciated that the activation of telomerase that occurs following chemo- or radio-therapy can alter the risk vs. benefit ratio of these treatments. That is, if the treatments result in the activation of telomerase in those cells that survived the primary treatment, they could become immortal due to the lengthening of the telomeres. Therefore, inhibiting the activation of TA would be a very useful approach in controlling tumor growth and many investigators are synthesizing and evaluating agents to inhibit TA for this purpose. Whereas telomerase activation and its effect on maintaining the length of the telomeres are protective to normal cells, both features are highly detrimental when attempting to induce lethality in cancer cells.

During normal cell division, when the cell reaches its finite life span, its telomeres are degraded. However, in human cancer cells, telomeres are continuously replenished by the human telomerase reverse transcriptase enzyme (hTERT), which is a subunit of telomerase. Thus, the activation of hTERT is problematic because it increases the resistance of cancer cells to various therapies. Many studies have shown the activation of hTERT as a factor in the treatment resistance to ionizing radiation; similarly, hTERT increases the resistance to chemotherapeutic agents. Therefore, numerous scientists are also investigating the use of telomerase- or hTERT-inhibiting agents to improve the efficacy of radiation or chemotherapy treatments. Among these drugs is tetra-(N-methyl-4-pyridyl)-porphyrin (TMPyP4) that binds to and stabilizes G-quadruplex (GQ) structures both in DNA and within the telomeres.

In DNA, the formation of a GQ structure in the promoter region of the c-myc oncoprotein is kinetically favored. Mutations occurring during chemo- or radio-therapy were shown to increase c-myc transcriptional activity 3-fold. Such over-expression results in gene amplification (e.g., multiple copies of c-myc), the formation of extra-chromosomal elements, chromosome breakage, deletions, increased aneuploidy, and polyploidization; all of these consequences demonstrate the instability caused to the genome by c-myc over-expression. Because TMPyP4 stabilizes the c-myc GQ, it can suppress its transcriptional activity and over expression. Of relevance is the fact that the hTERT gene, which encodes the catalytic subunit of telomerase, is also transcriptionally regulated by c-myc. Therefore, the stabilization of c-myc by TMPyP4 would additionally cause a decrease in hTERT levels and a reduction in telomerase activation (Papanikolaou V. et al., 2011, *Int J Radiat Biol* 87, 609-621), increased hTERT and TA was shown after irradiation of breast cancer cells and resulted in increased survival of the cells. This study showed that the HER2 receptor mediated hTERT expression through the sequential induction of nuclear factor kappa-light-chain-enhancer of activated B cells (NF-κB) and c-myc.

It may therefore be hypothesized that the radiation-induced mutations increased c-myc transcriptional activity and resulted in its over-expression, thereby increasing hTERT and telomerase activation as is discussed later. Therefore, the stabilization of GQ structures at the c-myc promoter locus could offer a very important contribution to cancer treatment.

Although several telomerase-inhibiting drugs have been synthesized, experimental results using said drugs have indicated that they are of limited efficacy. In this regard, the present inventors have now found that this problem is at least in part due to the rapid clearance of hydrophilic agents (for example the aforementioned TMPyP4) from the tumor. It appears that inhibition of the telomerase enzyme requires the continuous presence of the inhibitor in the tumor over the long term.

Various uses of porphyrins in treatment of cancer have been disclosed in WO03/063757. Porphyrins, such as metalloporphyrins of indium, gadolinium, platinum, palladium and gold, have been implied as Auger emitters, useful in conjunction with radiotherapy, such as brachytherapy.

A large number of controlled-release drug delivery compositions and devices have been described in the prior art. One such prior art publication (U.S. Pat. No. 6,206,920) discloses and teaches an in-situ forming injectable implant composition comprising poly(lactic-co-glycolic acid) copolymer (PLGA) in a solvent which is glycofurol.

U.S. Pat. No. 5,366,734 describes the combination of polylactide and a pharmaceutically active ingredient for the continuous release thereof in the form of a solid implant.

WO2011/071970 describes a combination of PLGA and porphyrins for photodynamic therapy.

It may be appreciated from the foregoing that there is a pressing need for a long-term, controlled delivery system that is suitable for use with telomerase-inhibiting agents.

BRIEF DESCRIPTION OF THE DRAWINGS

FIG. 11. PdTMPyP4 concentration measured in gelatin base over 9 days.

FIG. 12. The cumulative release of PdTMPyP4 from device over 52 days is exemplified. Release appears to be more rapid during the first month, and is subsequently more gradual. Release is also related to the weight of the device. The heavier the device, the greater is the released concentration.

DETAILED DESCRIPTION OF PREFERRED EMBODIMENTS

Figure 1:
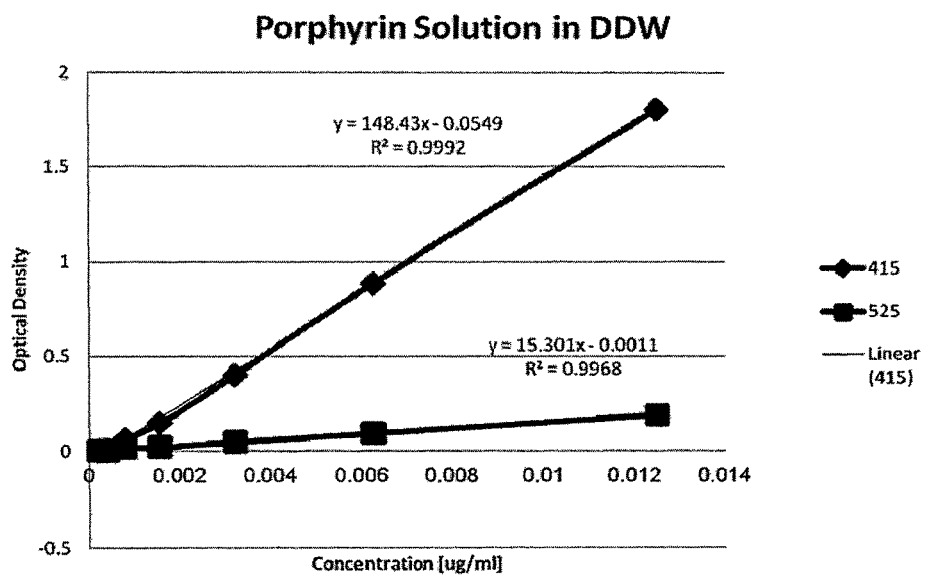
FIG. 1. Standard curve PdTMPyP4 absorbance as a function of PdTMPyP4 concentration as measured in double-distilled water.

The present invention provides a technical solution to the problem of providing a delivery system suitable of the controlled release of telomerase-inhibiting agents over long periods of time within tumor tissue. Without being bound by a specific theory, it should be noted that, in the case of the beneficial action of telomerase inhibition, the long term release is important for inducing the death of tumor cells. It may not be sufficient to inhibit telomerase over the short term because if inhibition is not continuous, telomerase is rapidly activated and telomeres lengthen again.

The present invention is primarily directed to a composition and device suitable for the long-term, controlled release of one or more telomerase-inhibiting agents into tumor tissue, wherein said device comprises one or more said telomerase-inhibiting agents and one or more polymer or copolymers capable of producing long-term controlled release of said agents.

In all aspects and the embodiments of the presently disclosed subject matter, the device is solid. The device may be suitably shaped such that it can be readily inserted into the tumor. There are various means of insertion of the implant into the tumor by implanting or injecting.

The solid device may be prepared and used in a variety of shapes and sizes. In one aspect, the solid device comprises a plurality of particles. Generally, the shapes and sizes of the device or of the particles thereof are chosen such as to enable direct delivery into the tumor. These include elongated forms of suitable dimensions for delivery to a tumor mass by means of local injection. The term "shape" is used interchangeably herein with the terms "form" and the like. According to some embodiments, the devices are in the form of a small, rod-like body, of dimensions similar to that of brachytherapy seeds. Additionally or alternatively, the devices are in form of micro- or nano-capsules or micro- or nano-particles.

Alternatively or additionally, the solid device is in a form of a tablet, e.g. a flat disc.

In some particularly preferred embodiments, the telomerase-inhibiting agent is a porphyrin, particularly a metalloporphyrin. In their most general form, metalloporphyrins have the following formula:

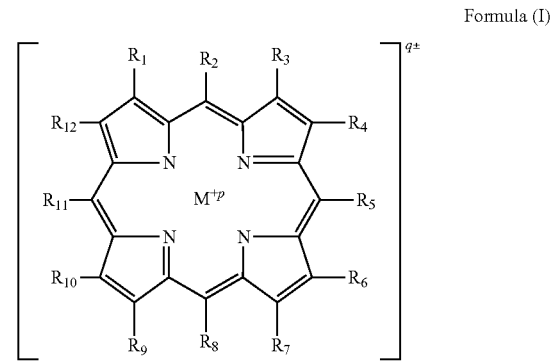

Formula (I)

wherein $R_1$-$R_{12}$ indicate same or different various substituents. Preferred are porphyrins substituted at the meso positions, i.e., where the eight β positions on the pyrrolic rings are all hydrogen atoms and the four meso positions (correspond to the methine bridges) are, for example, optionally substituted aryl or heteroaryl groups.

The metal $M^{p+}$ is usually an ion of a heavy metal. Within the scope of this disclosure, unless the context clearly dictates otherwise the term "heavy metal" should be construed to indicate a metal generally having an atomic number between 35 and 85, and which, following suitable activation, is capable of exhibiting the Auger effect, as discussed below. Preferably, the heavy metal is selected from the group consisting of palladium, platinum and indium. The heavy metal may be in a suitable chemically favorable oxidation state (+p) to produce the heavy metal ion with corresponding charge. The examples of such ions may be $Pd^{2+}$, $Pt^{2+}$ and $In^{3+}$.

For example, the metalloporphyrins may be substituted with the following groups on the meso positions (R2, R5, R8 and R11):

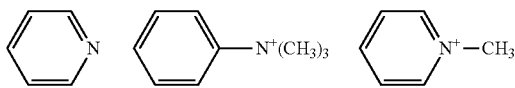

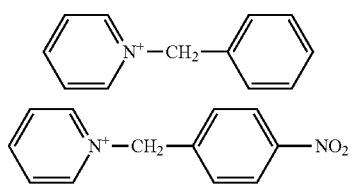

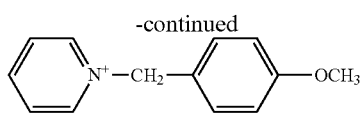

One class of meso-substituted metalloporphyrins which is suitable for use according to the invention is [M$^{p+}$-meso-tetra(N-methyl-4-pyridyl)porphyrin], which are designated herein MTMPyP4, and in particular, the palladium-containing compound (referred to hereinafter as PdTMPyP4). It should be noted, however, that, the metal-free compounds (designated H2TMPyP4), though less preferred, can also be used.

Another class of metalloporphyrins includes positive anilinium type porphyrins, i.e., where the meso positions (R2, R5, R8 and R1) are substituted with positively charged N, N, N-trialkyl anilinium of the formula:

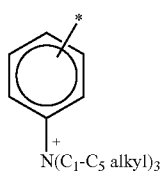

wherein the bond indicated by asterisk signifies the linkage to the porphyrin system.

The synthesis of various porphyrins and their conversion into metalloporphyrin can be accomplished according to known procedures. For example, the synthesis of meso-tetra-(N-methyl-4-pyridyl)-porphyrin was described by Hambright et al. (Inorganic Chemistry, 1970, 9(7), pp. 1757-1761). The synthesis of positive anilinium type porphyrins of the general formula:

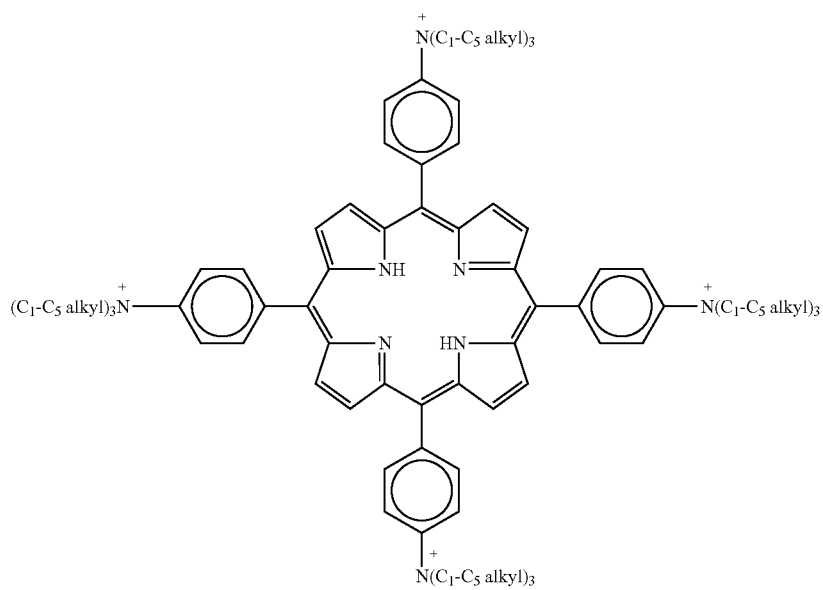

was described in Indian J. Chem, 15B, pp. 964-966, 1977.

Suitable porphyrins which demonstrate good telomerase inhibition are described by Shi D F, et al. (Journal of medicinal chemistry. 2001; 44:4509-23).

Synthesis of metalloporphyrins from the corresponding metal-free compounds is also described by Pasternack et al. (Inorg. Chem., 1990, 29, 4483-4486) and by Borsch (http://arxiv.org/ftp/arxiv/papers/1002/1002.1023.pdf). In general, the metal-containing complex can be prepared by reacting an excess of metal salt, for example, a chloride salt, with the porphyrin in an aqueous solution under stirring at reflux temperature. The complex may be precipitated with $NaClO_4$ or $KClO_4$. The solid is recovered by filtration, and the porphyrin perchlorate salt is treated to form water soluble chloride salts.

As indicated hereinabove, the controlled-release device of the present invention is capable of allowing controlled release of telomerase-inhibiting agent over a long term period (such as several days to several months). It has been found by the present inventors that the poly-(lactic-co-glycolic acid) copolymer (PLGA), with a weight ratio between the lactic and glycolic moieties, for example, 50:50, is especially capable of functioning as a long-term controlled release polymer when appropriately combined with metal-containing porphyrin compounds and incorporated into a controlled-release device of the present invention. Thus, in particularly preferred embodiments, the drug delivery device comprises one or more porphyrin compounds, e.g. a metallo-TMPyP4 (MTMPyP4) (for example, M=Pd, Pt or In) or other porphyrin which exhibits telomerase activity inhibition, together with PLGA, wherein the device is a solid implant.

The loading of the active ingredient in the solid device is usually described in weight percentage, i.e. mg drug per 100 mg of the implant device weight. The loading in the solid device of the invention may vary from 0.001% w/w to 70% w/w, e.g. 5-50%. The preferred range of the loading may be within any of the values there between, dependant on the nature of the drug and on the specific formulation. For example, for the tablet (disc) preparation the loading can be any amount that will not significantly affect the mechanical properties of the disc, e.g., is from 0.001% to 70%; for the multiparticulate formulation (nanoparticles powder) the loading is between 0.001% and 15%; for rod-shape device the loading is between 0.001% and 70%, e.g. 1% to 50%, 10% to 50%, or from 15% to 30%.

In addition to its suitability for long-term controlled release of active agents, PLGA has also been found by the present inventors to be combinable and compatible with a metalloporphyrin, such that the combination can be processed and isolated in a stable solid form, for example, as flat tablets, micro- or nano-particles, or in solid elongated forms of suitable dimensions for delivery to a tumor mass by means of local injection or insertion during a surgical procedure.

Additionally or alternatively, PLGA 50:50 may not be the only polymer suitable for the devices of the present invention. Copolymers of lactic-co-glycolic acid having different ratios can also be used, in the range from 10:90 to 90:10, for example 75:25 which is commercially available. As readily appreciable by a skilled artisan, the various PLGA copolymers exhibit varying in-vivo degradation rate, thereby controlling the release profile of an active material incorporated therein. The molecular weight of the copolymer may also vary within a broad range, e.g. from 10,000 to 100,000, although other MW-copolymers may be also suitable.

Other biodegradable polymers, however, may also be suitable for the same purpose. Examples of such biodegradable polymers can be found in the manuscripts familiar to the skilled artisans, such as, for example, Handbook of Biodegradable Polymers, Domb, Kost et al, 1998 by CRC Press, ISBN 90-5702-153-6; Handbook of Biodegradable Polymers: Isolation, Synthesis, Characterization and Applications, Leidlein and Sisson, 2011, by Wiley, ISBN 978-3-527-32441-5; and others.

One aspect of the invention is therefore a process for preparing a solid device comprising PLGA and at least one metalloporphyrin, comprising the steps of combining PLGA and said metalloporphyrin in a first solvent, placing the resultant mixture in a mold and recovering the desired solid composition optionally under anhydrous conditions. For example, the first solvent may be tetraglycofurol. The solidification of the metalloporphyrin-containing PLGA may be ultimately achieved by contacting the thickened mixture with a second solvent, in which PLGA is poorly soluble, e.g., anhydrous ethanol, allowing the removal of the first solvent. In some embodiments, the mold is in form of capillaries, wherefrom the thickened mixture is expelled into the second solvent, thereby allowing solidification in form of threads or truncated rods of desired thickness and/or diameter.

Similarly, the solid devices may be prepared as multiparticulate formulations, comprising micro- or nano-particles, pellets or granules. For example, the device may be in the form of a powder comprising micro- or nanoparticles each with PdTMPyP4 imbedded into each particle, e.g. PLGA-containing nanoparticles. Generally, the active material solution, such as of a porphyrin or of a metalloporphyrin, is dispersed in organic phase comprising the PLGA, and the resultant emulsion is optionally homogenized, for example, by at least one of a sonication, a microfluidizer, or a high-shear mixer processing. The homogenized emulsion is then dispersed in an aqueous medium and additionally homogenized to furnish a double emulsion. The double emulsion is then diluted with the aqueous medium and the organic solvent is removed to furnish a dispersion of micro- or nano-particles. The suitable organic solvents include, but are not limited to, ethyl acetate.

The solid devices may also be prepared by a further variety of methods known to a skilled artisan. These methods include compression/injection molding, as disclosed, for example, in U.S. Pat. No. 5,366,734 (to Zeneca Ltd). Generally, a pre-blend of an active material and the PLGA is prepared using solvent-casting techniques (dissolving or dispersing the drug and the polymer in a mutual solvent, i.e. dioxin-water, and casting the mixture on a substrate, allowing to dry and form a polymeric film with the drug dispersed therein). The pre-blended material may be homogenized by several consecutive molding and grinding steps, and a final mold is received by compression molding at a suitable shape and thickness.

The methods may also include extrusion, as disclosed ibid. Generally, the polymer is pre-processed for homogeneous blend, for example, by solvent-casting technique, or by lyophilizing the solution of PLGA in a suitable solvent, for example, glacial acetic acid, to furnish polymer powder. The powder is blended with the drug and the blend is extruded under pressure at an elevated temperature, for example, 70° C., to a suitable shape, for example, a 1-mm rod, which is further processed to a desired target weight. Alternatively, a mutual solution of a polymer and a drug is freeze-dried and the resultant blend is compression-molded to furnish an implant of suitable dimensions. As another alternative, the drug and the polymer can be pre-granulated, according, for example, the disclosure of WO publication 2000/33809, (to Mediolanum Farmaceutici S.P.A.). Solid devices may also be prepared in form of tablets of various shapes and sizes, by the techniques of tablets compression as known in the art.

In all the aspects and embodiments of the present invention, the drug is released from the devices at a controlled rate, characterized by a long-term duration. The long-term duration, as disclosed herein, should be at least a number of days that provides for telomere shortening after the initial telomerase inhibition and will vary according to the type of tumor, the forms in use and the dimensions thereof. During this time interval the drug is continuously released, meaning that between two consecutive samples there is an incremental amount of drug liberated from the device. The incremental amount is usually dependent on the total dosage of the drug, its potency and clearance characteristics from the tumor milieu. It is therefore possible to describe the percentage released from the device during a sampling interval. Generally, the incremental amount will preferably be the quotient of the 100% (or the total releasable amount) by the release duration, expressed in the units of time. In some embodiments, the release profile may be characterized with a burst initial release. In these cases the incremental amount is preferably the quotient of the difference of the total amount releasable and the burst release, by the release duration.

In another aspect, the present invention provides a method for the controlled delivery of one or more telomerase-inhibiting agents into a tumor, wherein said method comprises the steps of injecting into a tumor solid implants with the shape and dimensions as described herein, comprising a telomerase-inhibiting agent embedded within a matrix that enables the continuous controlled release of said agent over a long term time period (for example, a PLGA matrix).

As described herein, the terms "tumor" or "cancer", as used interchangeably in the current disclosure, include solid proliferative neoplastic diseases. The tumors responsive to the therapy with the devices of the present invention include, but not limited to, prostate cancer, ovarian, head and neck cancer, cervical cancer, breast cancer, and glioblastoma. In some of these tumors, the activation of telomerase will be the main contributing factor responsible for telomere elongation and immortalizing the cancer cells. The TMPyP4 component of the present invention is useful in preventing this. However, some of these tumor types preferentially use the homologous recombination modality to elongate telomeres (neurological origin, such as glioblastoma). The Pd tag on the TMPyP4 molecule, when used together with iodine-125 brachytherapy seeds, is aimed to fragment any elongated telomeres and prevent immortalization.

In yet further aspect, the present invention provides a method disclosed hereinabove for the controlled delivery of one or more telomerase-inhibiting agents into a tumor, wherein said method comprises inserting into a tumor a solid device, for example, in a form of a disc. The diameter of the disc can vary according to the needs of the specific tumor size, type and location. The diameter of the disc may be as low as 1 mm or as high as 30 mm in diameter with a thickness as low as 0.5 mm or as high as 5 mm and may be of any value therebetween, for instance, the dimensions of the exemplified hereinafter disc is 13 mm in diameter on 5 mm in thickness.

In a further aspect, the present invention provides said method wherein the solid device is in a form of multiparticulates. The diameter of the particles may vary from 2 nm to microns up to several mm.

In a more preferable aspect, the present invention provides said method wherein the diameter of said particles is within the range of 50 nm to 500 nm, preferably within the range of 100 to 200 nm.

In a still further aspect, the present invention provides said method wherein the solid device is in a form of rods. The rod synthesis is extremely flexible. The dimensions of said rods may vary from 0.1 mm in diameter up to 10 mm and up to several cm in length.

In one preferred embodiment of this method, the telomerase-inhibiting agent is TMPyP4 (either untagged or tagged with palladium), and the matrix comprises PLGA.

According to some particularly preferred embodiments of the invention, the tumor region is also irradiated by means of a radiation source having an energy output capable of activating the heavy atom that had been tagged to the telomerase inhibitor to emit Auger electrons therefrom.

Auger effect, as referred to herein, is the generation of an energy quantum equal to the difference in the energetic levels of an upper and a lower electron orbital of a heavy metal, following externally-effected removal of an electron from the lower orbital and subsequent sinking of an energetic electron into a more energetically favorable position in a lower orbital. The incorporation of the Auger emitter in a metalloporphyrin may provide targeting of the radiotherapy to the G-quadruplexes inside the cancer cell DNA, thereby increasing the efficacy of anticancer treatment and diminishing the probability of the side effects. An Auger emitter inside the DNA-bound porphyrin provides the source of deleterious radiation inside the cancer cell, and thereby the damage to the surrounding healthy tissue is minimized, in comparison to the conventional external-source radiotherapy.

Most preferably, the radiation source produces a photon (X- or γ-ray), the energy of which is above the M-, L- or K-shell energies of said heavy metal. The radiation source is implanted near or in the body region to be treated, and it comprises one or more radioactive isotopes generating the desired energy for removing the primary electron from an inner electronic shell of the heavy metal. The radioisotopes are encapsulated within a casing, which is preferably in the form of a closed, cylindrically shaped canister, known as "seed". Thus, in some preferred embodiments of the invention, use of the solid devices of the present invention further comprises co-administration of a brachytherapy seed which also serves as an activator for the Auger emitter. For example, iodine-125-containing brachytherapy seeds, which are commercially available, may be used. Additionally or alternatively, the brachytherapy seeds may contain any of samarium-145, thulium-170, palladium-103, or a mixture of iodine-125 with iodine-127. Thus, the simultaneous placement of the metalloporphyrin-containing PLGA implants of the invention and, for example, the iodine-125 brachytherapy seeds that induce an Auger effect forms are particularly preferred. By inserting the device and seed simultaneously, the present invention offers a potential one-step outpatient treatment procedure wherein the device and seed are implanted directly into the tumor, and act immediately to reduce the tumor size and prevent its regrowth, then degrade naturally so removal is unnecessary.

Without being bound by a specific theory, the inventors additionally believe that because PdTMPyP4 binds to G-quadruplex (GQ) configurations both in the promoter regions of oncogenes and in the telomeres, the radiation from, e.g. the iodine-125, seeds may provide a 'check and balance' mechanism that will enable the telomeres to shorten as a result of telomere fragmentation by the radiation, which may be lethal to the cells in presence of a telomerase inhibitor. The preferred embodiment the solid devices may have dimensions, similar to that of the brachytherapy seeds; that is from about 4×0.8 mm whose insertion into the tumor will encourage photo-activation between the drugs and appropriate energy sources. The insertion of the devices into the tumor may be achieved by use of a blank veterinary chip implanter for animal work or through prostate brachytherapy guide tube or other sharp modalities that allow penetration into the tumor.

The following sections will present experimental methods and data in which the various aspects of the presently disclosed invention are exemplified.

EXAMPLES

Example 1—Preparation of the Solid Implants in Form of Rods

PdTMPyP4 was weighed and placed in a straight-sided glass vial. At a weight to volume (w/v) ratio of 0.18 PdTMPyP4:tetraglycofurol; the latter was added to the PdTMPyP4 and mixed by hand to ensure total incorporation of the powder within the liquid. The preparation was carried out under yellow light conditions and exposure of the mixture to air was kept to a minimum. Teflon coated stirring rods were added to the vial, the vial covered with two layers of Parafilm® and wrapped in aluminum foil. The covered vial was then centered on a magnetic stirrer at slow speed for at least 40 minutes to one hour and checked constantly to assure that no crusting occurs on the vial walls. The 5050 DLG 5E lactide/glycolide powder (SurModics Pharmaceuticals/Evonik) was weighed, placed in a glass vial and exposed to UV light under a sterile hood. Glass capillaries with an inner diameter of 1.15 mm+/−0.05 mm were also placed under UV light. The DLG powder was added to the mixing vial at a w/v ratio of 0.25, the vial was resealed and stirred at slow speed overnight. The mixture was checked to ensure its homogeneity. The material was drawn up into a sterile disposable syringe using a 21 G sterile needle. Any bubbles that had formed in the viscous mixture were expelled and when the syringe was inverted. The glass capillaries were frozen in a dish of anhydrous ethanol at 0° C. The material was slowly injected into the capillary and the capillary submerged in anhydrous ethanol and placed in the freezer overnight. A trochar was used to expel the material from the capillary directly into anhydrous ethanol at or near freezing temperature. During and after expulsion the polymer solidified and became a biodegradable tube-like structure that can be easily handled. The material was removed from the ethanol, placed on a dry dish, and cut into rods 3 mm in lengths, with a scalpel blade.

Figure 14:
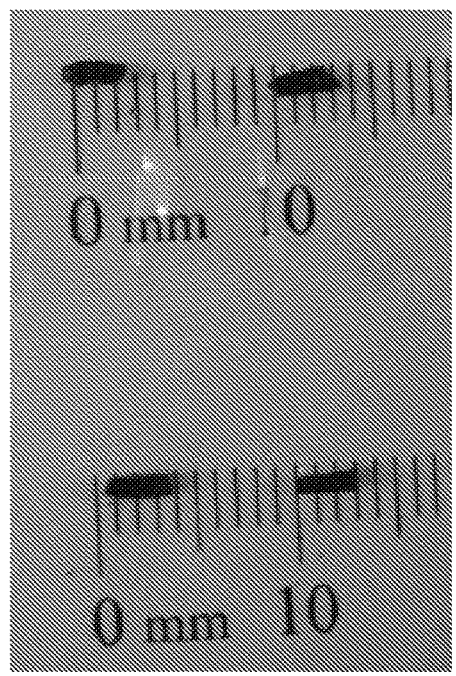
FIG. 14. The device of the invention in the form of small, solid rod-like bodies is exemplified.

Each of these 3×1.5 mm solid rod-like structures (shown in FIG. 14) is an independent device that can be inserted into medium where the controlled release of PdTMPyP4 is available for long term in vitro experiments. They can also be placed in the beveled edge of a trochar and inserted into tumor using a stylette.

Example 2—Preparation of the Solid Implants in Form of Micro- or Nano-Particles

The preparation of the micro- or nano-particles was performed using the solvent removal technique from polymer-stabilized water-in-oil-in-water double emulsion. PLGA (50:50), 200 mg, was dissolved in 2 mL of ethyl acetate. The encapsulated material, PdTMPyP4, 1 mg, was dissolved in 1 ml of double-distilled water. A 20 µl aliquot of the aqueous solution was vigorously dispersed in the organic phase for 30 sec using ultrasonic bath, (MISONIX, 600 W), 20 kHz at 40% amplitude, until the mixture obtained a characteristic milky appearance. A 5-% solution weight per volume of polyvinyl alcohol, 88% hydrolyzed, MW about 88 kDa, was prepared by dissolving the PVA in water. The emulsion was added dropwise into 4 ml of the 5% PVA solution up to a period of 60 seconds. An additional step of sonication was performed, at 40% amplitude for 10 sec in continuous mode. Three cycles were performed with several seconds break there between, while preventing the temperature elevation by placing the mixture on ice during the breaks. Immediately upon completion of the sonication the mixture was introduced into 100 ml of vigorously stirred 0.5% solution weight per volume of PVA, and was left stirring for at least 3 hours at room temperature to evaporate the organic phase. Harvesting of the particles was done by using centrifuge at 20000 rpm (about 10000 g) for 45 min. After removing the supernatant the pellet was redispersed in 4 ml of double-distilled water to wash the particles, and further centrifuged for 20 minutes at 20000 rpm. The washing was performed twice in the same manner. The pellet was lyophilized by freezing in liquid nitrogen and dried under vacuum for about 48 hours. The freely flowing powder was stored at −40° C. until use.

Example 3—Exemplary Preparation of the Solid Implants in Form of a Tablet

A tablet was prepared using neat active material and PLGA powder. No lubricant was needed under this procedure.

PdTMPyP4 (2 mg), was accurately weighed on semi-micro analytical balance, and placed into a suitable mortar. Onyx mortar for sample preparation for infra-red spectroscopy was used. PLGA, 98 mg, were accurately weighed and placed into the same mortar. The powders were ground together for to ensure homogeneous distribution of the active material.

The powder blend was placed in a 13-mm diameter die and compressed with the punched at the pressure of above 3 atm for about 5 minutes. After releasing the pressure the tablet was removed from the die. The obtained thickness of the tablet was about 5 mm.

Examples 4-11

Materials and Methods

Agents:

Palladium-tagged tetra (4-N-methylpyridyl) porphyrin (PdTMPyP4), purchased from Frontier Scientific, and hydrogen-tagged tetra (4-N-methylpyridyl) porphyrin H2TMPyP4 (courtesy of Professor Peter Hambright) were dissolved in complete RPMI 1640 medium at concentrations ranging between 0.05 and 0.2 mg/ml.

The full growth medium comprised RPMI 1640 medium (Biological Industries, Bet Haemek, Israel), supplemented with characterized 10% fetal bovine serum (FBS-Hyclone), 2 mM 1-glutamine (Biological Industries, Bet Haemek, Israel), 50 µg/ml penicillin and 50 µg/ml streptomycin (Biological Industries, Bet Haemek, Israel).

To determine the most suitable concentration of the agents and time interval that would yield a similar response to the different agents, cells ($5\times10^4$), were treated with different concentrations of PdTMPyP4 or H2TMPyP4 dissolved in complete growth medium and incubated for 24 and 48 h at 37° C. in a humidified 5% $CO_2$ atmosphere. Because both drugs are very sensitive to white light, all studies were carried out under dimmed light conditions using amber glass, when necessary.

The L428 Hodgkin's lymphoma (HL)-derived cell line (DSM ACC 197) was gratuitously obtained from the laboratory of Prof J. Gopas, in the Departments of Immunology and Radiation Therapy at Ben Gurion University. The line was derived from a case of nodular sclerosis type HL case. The cells were grown in suspension in a 95% humidified environment at a temperature of 37° C., pressure of 5% $CO_2$, and maintained in the full growing medium. All experiments were carried out using these and KHJJ murine mammary adenocarcinoma line, derived from a primary mammary tumor arising in a BALB/c mouse after implantation of a hyperplastic alveolar nodule. (S. C. Rockwell et al *Journal of the National Cancer Institute* 49, 735-749 (1972).

Under the described conditions, the cells generally double their population within 30 h. In order to assess whether telomerase inhibition was an important factor in inducing cell lethality, the experiments were designed to encourage and sustain an exponential growth rate throughout the duration of the experiment. This required splitting the cells in advance of their reaching their maximum tolerable density of $1.5\times10^6$ cells/ml or before other factors, such as nutrient depletion, affected their growth. Once the cell count from any of these treatments approached this value, flasks from all treatments were split, regardless of whether a split was necessary. In those flasks where the cell counts did not approach the maximum tolerable density, and the cells were split, occasionally there was a lag in the growth rate that picked up over time once the medium became sufficiently conditioned.

Example 4—Incorporation of PdTMPyP4 in DNA

Figure 8:
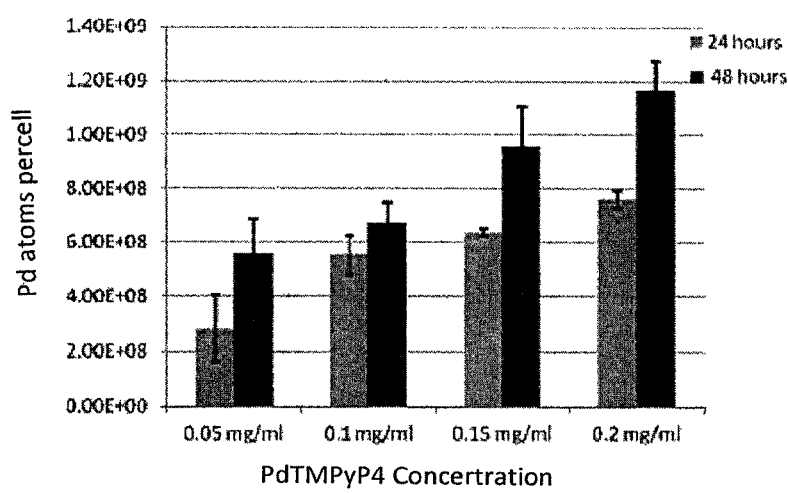
FIG. 8. Comparative uptake of graded concentrations of PdTMPyP4 in the DNA fraction of cells. Cells were incubated for 24 h and 48 h at the PdTMPyP4 concentrations indicated.

PdTMPyP4 was dissolved directly into medium as described above. After incubation with graded concentrations of PdTMPyp4 added to the medium for 24 or 48 h, the DNA was extracted and digested. To determine if PdTMPyP4 would accumulate in DNA as was shown for naïve TMPyP4, inductively-coupled plasma-mass spectrometry (ICP-MS) was used to measure the amount of palladium in cellular DNA. Details of the methods used to extract the DNA fraction and prepare the samples for ICP-MS are given in Laster B H, et al. Brachytherapy. 2009; 8:324-30. The results are shown in the FIG. 8.

The results of the study validate that the Pd tag does not alter DNA uptake of the porphyrin. The increased uptake with time and concentration suggested that an intratumoral long-term, continuous release approach to drug delivery could be highly suitable because it would facilitate the accumulation of PdTMPyP4 in tumor DNA. Additionally, the measured uptake of about $10^9$ Pd atoms in the DNA of the cell, when converted to moles (about $1.7 \times 10^{-14}$ mol) approximates the number of TMPyP4 moles that were also incorporated in DNA at the concentrations and time intervals indicated. To the best of our knowledge, these measurements may be the first to approximate the intracellular uptake of given concentrations of TMPyP4 overtime.

The incubation of L428 cells with identical concentrations of TMPyP4 demonstrated different behaviors depending upon whether the tag was H2 or Pd.

Figure 9:
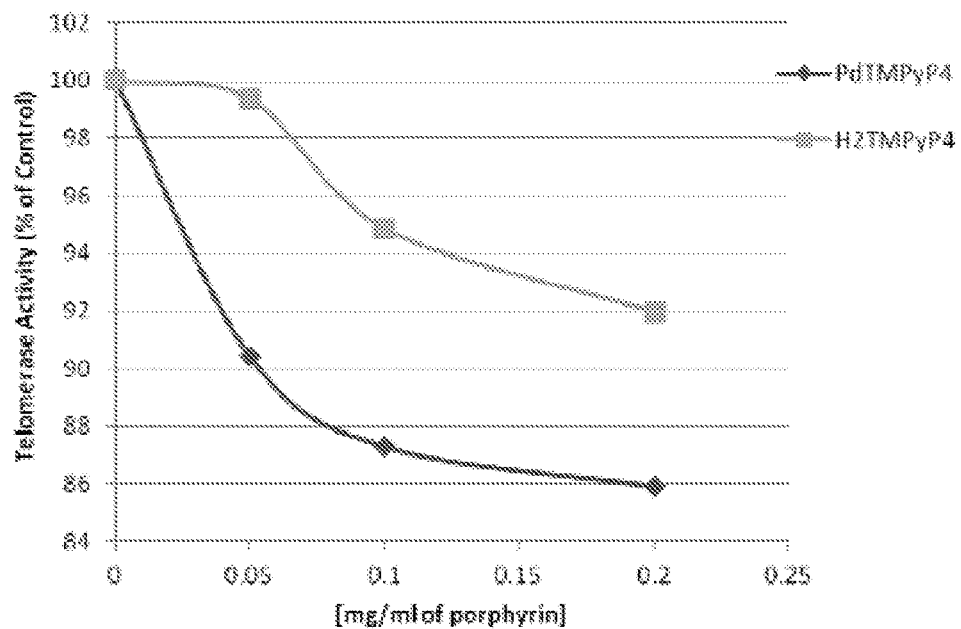
FIG. 9. Telomerase activity as a function of porphyrin concentration, after a 24 hour incubation. Results were normalized to the telomerase levels in untreated cells.
Figure 10:
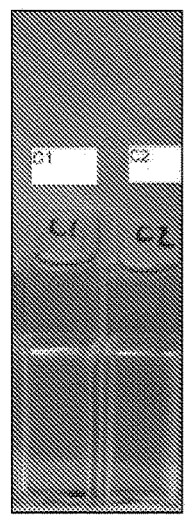
FIG. 10. Release of PdTMPyP4 after 30 days in a gelatin base. The device was imbedded in a thick gel layer at the bottom of the cuvette to keep the device in position. Weights of rods: C1=0.00191 g; C2=0.00196 g. Remnants of the degrading PdTMPyP4/PLGA device can still be observed in the bottom of the cuvette after 30 days.

Example 5—Evaluating the Effect of PdTMPyP4 or H2TMPyP4 on Telomerase Activation and/or Inhibition L428 cells were incubated for 24 h with graded concentrations of PdTMPyP4 or H2TMPyP4 dissolved in RPMI 1640 complete medium. The activation or inhibition of telomerase was measured using the Telomeric Repeat Amplification Protocol (TRAP) assay. The procedure is detailed in Tichon A, et al, Cytotherapy. 2009; 11:837-48. The results are shown in the FIG. 9.

Figure 5:
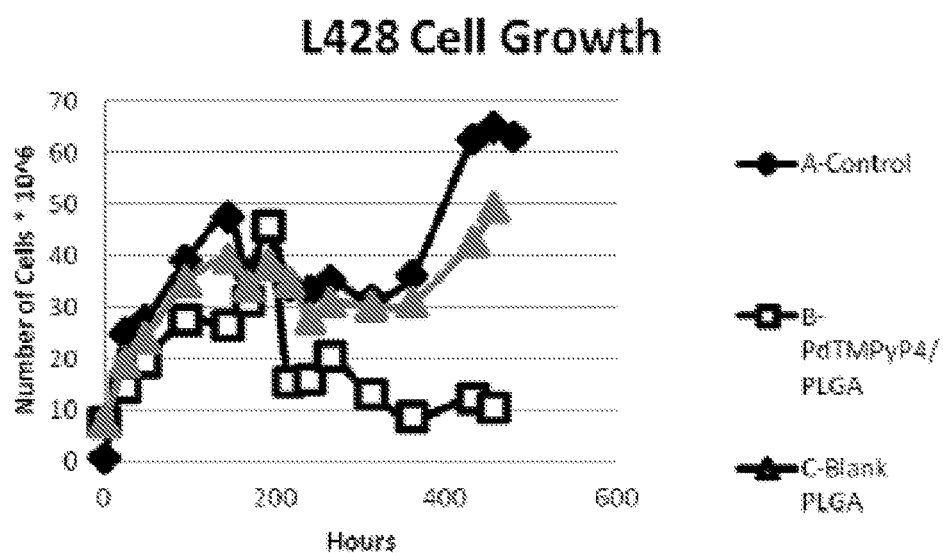
FIG. 5. Impact of different treatments on L428 cells after 456 hours (about 18 days). The same phenomenon shown in FIG. 4 can be observed here. Cells were split at 96 hours and 432 hours.

Measurements of telomerase activity in L428 cells after incubation with graded concentrations of H2TMPyP4 or PdTMPyP4 revealed a superior inhibition when the TMPyP4 inhibitor was tagged with Pd as opposed to H2 (FIG. 5). It has been suggested that a tag might impact on the configuration of the GQ when TMPyP4 acts as a ligand to the GQ and that the weight of the tag might be of positive benefit in stabilizing the GQ (Wei C, et al, 2006, Biochemistry, 45:6681-6691; Wei C, et al, 2009, Phys Chem Chem Phys 11:4025-4032; Georgiades S N, et al, 2010, Angew Chem 49:4020-4034). This would explain the superiority of PdTMPyP4 over H2TMPyP4 in preventing c-myc overexpression and hTERT stimulation of telomerase activation; however, the magnitude of the effect of addition of palladium to the molecule and considering merely the small addition to the molecular weight, without being bound by a specific theory, palladium atom may specifically contribute to GQ stabilization beyond the mere mass effect. This finding lends credibility to the idea that the tag may have a strong influence on the formation and functioning of the GQ, and opens the door for other high z atoms to be tagged to the porphyrin.

The binding of H2TMPyP4 to different GQ configurations was studied extensively (Mikami-Terao et al, Cancer Lett, 2008, 261:226-34) and showed that, depending upon the configuration of the particular GQ, two H2TMPyP4 molecules could be externally stacked at two ends of the parallel G-quadruplex, or H2TMPyP4 molecules could intercalate within their diagonal or lateral loop regions and at the intervals between two G-tetrads. The GQ binding characteristics differ for TMPyP4 (Colombo et al, Int J Oncol, 2005; 27:1053-9) and to the best of our knowledge, the binding characteristics of PdTMPyP4 to GQs have not yet been studied. Nevertheless, the data herein suggest that the efficiency of telomerase-inhibiting agents, whose actions are implemented as a result of their binding to GQ structures in DNA, may be dependent upon the actual binding characteristics of the molecules to the GQ structures as opposed to the mere fact that they bind.

Example 6A—Cell Response to Controlled Release of PdTMPyP4 from PLGA Rods into Medium In these experiments, PdTMPyP4/PLGA rods, manufactured as described in the Example 1, were used to release and maintain the continuous exposure of exponentially-growing L428 Hodgkin's Lymphoma cells to PdTMPyP4 throughout the 8 day experiment. To maintain and encourage exponential growth, cells were split before they neared their maximum density $1.5 \times 10^6$ cells/ml. Precautions were taken, in advance, to prevent the dilution of the drug during cell splitting by placing the rods into the medium that would be used when splits were required. Cells were initially seeded into each of 3 different treatment flasks at a cell density of $3.0 \times 10^5$ cells/ml in a volume of 25 ml. The cultures were split at 120 and 192 hours. The flasks consisted of:

A—RPMI 1640 complete medium;
B—RPMI complete medium with 2 gel-coated PdTMPyP4/PLGA rods, manufactured as described in the Example 11 below; and
C—RPMI complete medium with 2 blank PLGA rods, manufactured according to the Example 1 without the active material.

Fourteen 'medium-transfer' flasks were prepared in advance for use during the splitting of the flasks. Twelve (6 each) of these contained 25 ml of complete medium and either 2 PdTMPyP4/PLGA rods or 2 blank PLGA rods.

Two additional flasks contained 25 ml conditioned medium were prepared in advance, by removing from previously grown cells and sterilizing, and whereto either PdTMPyP4/PLGA or 2 PLGA rods were added. This approach permitted the same exponential growth conditions for all treatments even when the flasks were split. Under the described conditions, the addition of 30% conditioned medium to fresh medium sustains an exponential growth rate which was one of the experimental goals.

Figure 4:
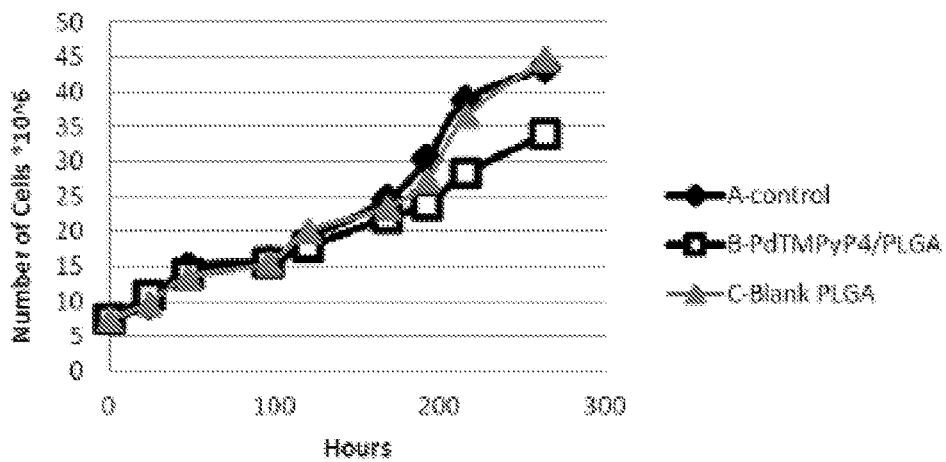
FIG. 4. Impact of the different treatments on the survival of L428 cells after about 8 days. Cells were split at 120 h and 192 h.

When cells in either flask A, B, or C neared their maximum cell density and required splitting, all flasks were split at this same time and medium from the transfer flasks was added to both the original and new flasks to restore the volume to 25 ml. A 3-ml aliquot of cells was removed from the flasks containing the suspension cells and was counted on a daily basis using a hemocytometer and trypan blue exclusion. The volume removed was replaced with the pretreated medium. Optical density was measured daily, and concentration calculated as described below in Example 10. Cells in each of the split dishes were counted, and counts from all flasks were combined to yield the total number of cells. By combining the cell counts from the split flasks, and using the total cell number, technical errors in counting the cells from the different flasks were reduced. The results are shown in FIG. 4.

Example 6B—Cell Response to Controlled Release of PdTMPyP4 from PLGA Rods into Medium The experiment of the Example 6A was repeated for the longer period of 19 days.
The cell cultures were split after 96 and 432 hours.
The results are shown in the FIG. 5.
Results of an 8 day experiment where the exponential growth of L428 cells was sustained for up to about 200 h despite the continuous presence of the PdTMPyP4 inhibitor. The cultures were split at the 120 h and 192 h time points. The method of splitting the cells and the advance preparation of the medium proved very successful in sustaining the exponential growth of the L428 cells and assuring their continuous exposure to PdTMPyP4. Beyond about 200 h, there was a slight decrease in the survival of those cells exposed to the PdTMPyP4 compared to those untreated or exposed to the blank PLGA. By the end of the 264-h experiment, the PdTMPyP4 cell number was lower compared to the other treatments. In this experiment, unlike the untreated control cells and those with the blank device, the curve for PdTMPyP4 cells began to shift to the right after about 200 hours, suggesting that some mechanism became operative and affected the exponential growth rate of the cells with PdTMPyP4. It seems that at, or around this time, the earlier inhibition of telomerase may have had the opportunity to shorten the telomeres. Without being bound to a specific theory, the dynamics of telomerase and its influence on telomere lengthening may be non-linear. The shortening of the telomeres after telomerase inhibition may also be non-linear and dependent on the initial length of the telomeres and the extent of their progressive shortening during telomerase inhibition.

The results of the 19-day experiment indicate the initial exponential growth behavior in presence of PdTMPyP4. The slight lag in the growth of the cells with the PdTMPyP4/PLGA device, and those with the blank device, following the split is probably due to the lower number of cells in each flask after the split. The cells respond much faster when the medium is conditioned and, despite the addition of 30% conditioned medium, there was a growth lag with all treatments after the split. Whereas the growth rate increased in the untreated controls and those grown in medium with the blank PLGA device, there was a sudden decrease in the cells exposed to PdTMPyP4 at about 200 h (8 days). The decreasing cell numbers after PdTMPyP4 exposure at 200 h in the experiments suggest that, at least with the L428 cell line, the shortening of telomeres requires 1 week before lethality becomes evident. From this point and throughout the remaining 11 days of the experiment, the PdTMPyP4 cell number was a factor of 5-6 times lower than with the other treatments. These findings demonstrate the lag between the time that telomerase was inhibited and the time that the telomeres shortened sufficiently to enable cell senescence and lethality.

PdTMPyP4 induces L428 cell lethality about 8 days after telomerase inhibition. After incubating L428 cells according to their various treatments, a decrease in cell survival is observed only with PdTMPyP4-treated cells, compared to untreated controls or those without PdTMPyP4 in the rods. It occurs after about 1 week of incubation with the drug. The same 1 week delay is seen where the cells did not recover despite the lengthier duration of the experiment. The rapid decline in the numbers of PdTMPyP4-treated cells after about 1 week suggests that it may have taken about 1 week of continuous telomerase inhibition by PdTMPyP4 before the telomeres shortened sufficiently for L428 cells to activate death pathways. This finding with L428 cells appears to be compatible with those of others who had also demonstrated a lag time between telomerase inhibition and telomere shortening with different cell lines (Delhommeau F. 2002, et al, Oncogene 21:8262-8271).

Figure 6:
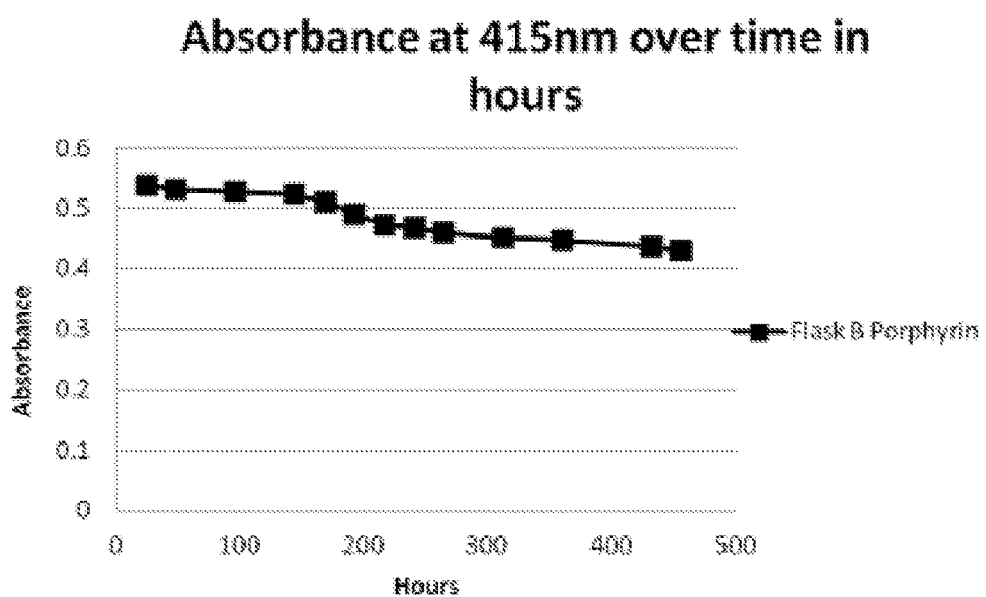
FIG. 6. Absorption spectrum of porphyrin release in medium over 18 days.
Figure 7:
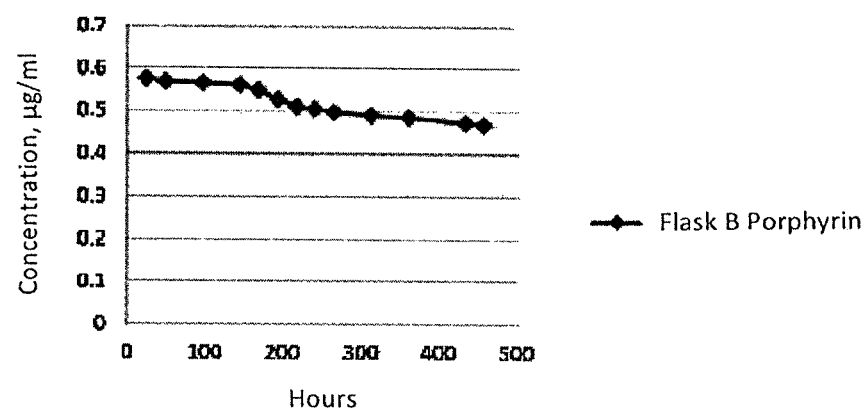
FIG. 7. Concentration of PdTMPyP4 release in medium over 19 days. The response of L428 cells to this concentration is shown in FIGS. 4 and 5.
Figure 15:
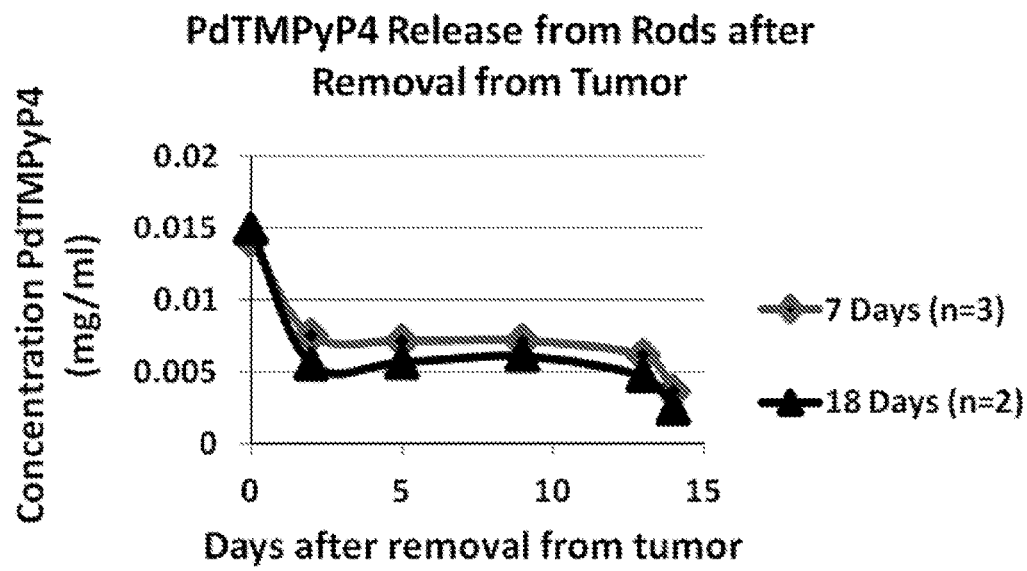
FIG. 15. Ex vivo study demonstrating PdTMPyP4 release in the saline environment for up to 30 days after the rods were removed from the KHJJ murine breast carcinoma tumors borne on the thighs of BALB/c mice.

The dynamics of telomerase and its influence on telomere lengthening is reported to be nonlinear (Blagoev K B, 2009, PLoS One 4:e4622). It is also postulated that the shortening of the telomeres after telomerase inhibition is likely to be nonlinear and reliant upon both the initial length of the telomeres and the extent of their progressive shortening during telomerase inhibition (Herbert B et al, 1999, Proc Natl Acad Sci USA 96:14276-14281). This suggests that these parameters would be important considerations in a clinical situation where telomere length differs among various cancer types. The FIG. 6 shows the measured absorbance values of PdTMPyP4 as a function of time over the 19-day experiment and how these values were used to calculate the concentration (FIG. 7). Unlike the increasing linear slope seen with the in vitro measurements, the shallow decline in the slopes in FIG. 6 suggests that the PdTMPyP4 released into the medium had slowly and gradually been taken up by the cells. This same phenomenon might also have applied to the reduced concentration measured after the removal of the rods from the tumor as shown in FIG. 15.

From the FIG. 6, it is clear that there was only a slight reduction in the drug concentration in the medium as the cells took up the drug suggesting that PdTMPyP4 would have been available for tumor cell uptake for an even longer period of time as was shown subsequently in the in vivo situation.

Example 7—Tumor Response to PdTMPyP4 Release

A KHJJ murine mammary adenocarcinoma tumor fragment (donor to host) (Rockwell et al. 1972, J Natl Cancer Inst 49:735-749) was implanted via trochar and stylette on the thigh of BALB/c mice as reported in Laster et al, 2009, Brachytherapy 8:324-330. When tumors grew to a volume of about 150 mm$^3$, two PdTMPyP4 rods, prepared as described in the Example 1, were implanted directly into the tumors of five mice using the technique described in Laster et al. 2009, for brachytherapy seed implantation. No treatment was given to the tumors of similar size in another group of five mice. Tumor dimensions were measured using a digital caliper, and its volume was calculated as described in Rockwell et al. 1972. The results are shown in the FIG. 13.

PdTMPyP4 release retards tumor growth. An in vivo study was carried out in which two PdTMPyP4/PLGA rods were implanted in the KHJJ adenocarcinoma as described above. Five other mice, bearing tumors of similar volume on day 0, were studied as controls (FIG. 7). The mean threefold increase of their initial volume at day 0, within a 5 days period, confirms the aggressiveness and rapid growth rate of this tumor model. However, its propensity for rapid growth was altered by the intra-tumoral insertion of the rods loaded with PdTMPyP4. Comparing the volumes of untreated and treated tumors at the same level of biological effect, about 750 mm³ (fivefold the tumor volume at day 0), this volume was reached on day 10 in the five untreated mice and on days 34, 41, 48 and 49 in four PdTMPyP4-treated mice, while the tumor in the remaining mouse practically regressed by day 40. The inability of the inserted rod to sustain the delay in tumor growth may be a consequence of the degradation of the rod after about 30 days and the reactivation of telomerase and renewed telomere lengthening when PdTMPyP4 was no longer released. On the other hand, tumor regrowth may also have been a function of the activation of the alternative lengthening of telomeres (ALT) mechanism that lengthened the telomeres.

Figure 13:
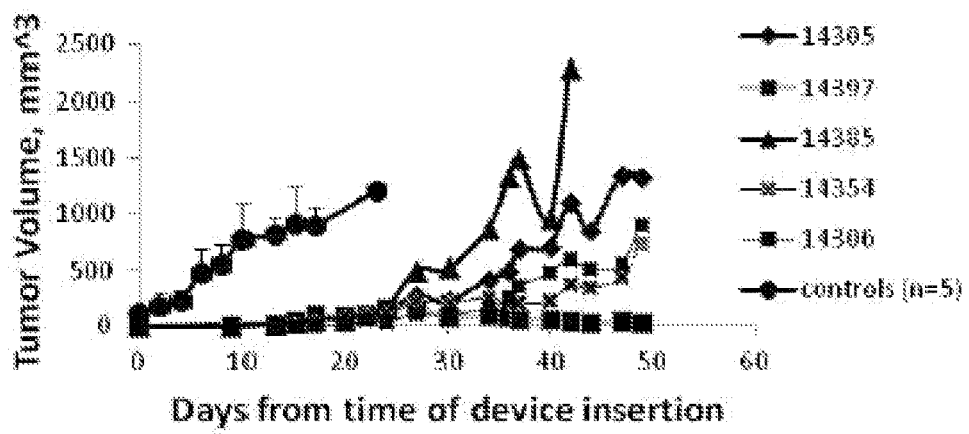
FIG. 13. The tumor growth rate following the insertion of the device of the invention is exemplified.

Tumor growth of untreated controls and mice with 2 inserted PdTMPyP4 devices per tumor. Tumor growth of each individual mouse with inserted devices is shown. At about day 24, the treated tumors began to show differences in their response to PdTMPyP4 release, as shown in FIG. 4. Comparing tumor growth in treated mice compared to untreated controls at the same level of biological effect (1000 mm³), it is evident that the inserted devices retarded growth. FIG. 13 compares the effectiveness of the PdTMPyP4 seeds in controlling tumor growth. Out of 5 mice, one tumor disappeared completely, 3 mice showed retardation in their growth rate by a factor of 2-2.5, and 1 mouse by a factor of 1.5 compared to untreated controls.

Example 8—Blood Plasma Concentrations in Response to Intratumoral PdTMPyP4 Release One PdTMPyP4 rod, prepared according to the Example 1, was implanted into the KHJJ tumor of each of 4 mice as described in the Example 7 above.

Blood was withdrawn from the junction of the submandibular/facial vein, centrifuged, and the clear supernatant removed, diluted 1:100 and measured in double-distilled water (DDW) as described in the Example 10 below. The results are shown in the FIG. 16. The Figure shows that negligible concentrations of PdTMPyP4 entered the blood stream and were transported in the blood plasma after the intratumoral insertion of a single rod in each of four mice. In those instances where the concentration in blood plasma peaked within the first week, it may have been due to trauma to the intratumoral vasculature during the rod insertion. By the second and third week, there was restoration of plasma levels to that on day 0 (prior to rod insertion).

Example 9—In Vivo PdTMPyP4 Release

PdTMPyP4 devices were removed from the tumors on either day 7 or 18 after intratumoral insertion, washed with DDW and placed in the normal saline to evaluate the residual release of PdTMPyP4 therefrom.

A burst of PdTMPyP4 release from the rod was observed immediately upon its immersion in fresh saline suggesting that PdTMPyP4 after the periods of 7 or 18 days, respectively, the material is still retained in the device and is releasable upon contact with extraction medium. This study confirmed that when the DDS is inserted into the tumor environment, it does not undergo rapid degradation, but appears to release PdTMPyP4 continuously at a gradual. The average weights of the rods were 0.0013 and 0.0007 g for the 7- and 18-day insertions, respectively, indicating roughly time-proportional degradation of the matrix in-vivo.

Example 10—Analytical Procedures and Results

Example 10A—Measurement of PdTMPyP4 Release in Gelatin Base

To assess whether coating the rods with gelatin would alter the optical density in measuring PdTMPyP4 release over time, a standard curve of PdTMPyP4 in gelatin was obtained. Titrated samples of known concentrations of PdTMPyP4 were mixed with a liquid consisting of 10 g gelatin, 35 ml glycerol and 9 ml DDW. Upon solidification, the optical density was measured using an Optizen POP UVvis spectrophotometer. To identify the most useful peaks, the titrated samples were scanned and peaks were evident at wavelengths of 415 and 525 nm. The greater intensity of the peak at 425 nm suggested it would be more useful to use this peak to determine the concentrations of unknown samples. A standard curve of absorbance as a function of PdTMPyP4 concentration was prepared, replicated and linear regression analysis performed in order to derive an equation that could be used to determine the concentration of unknown samples.

Example 10B—Measurement of PdTMPyP4 Release in DDW

Titrated samples of known concentrations of PdTMPyP4 were dissolved in DDW and optical density measured as described above. A standard curve of absorbance as a function of PdTMPyP4 concentration was prepared and replicated. Concentrations of PdTMPyP4 release in the studies presented here were calculated according to the formula derived by linear regression of the standard curve. To determine if the DDW standard curve would be appropriate for calculating the concentration of PdTMPyP4 released in RPMI medium, or if there would be competition at the 415 or 525 nm peaks, a spectroscopic scan of the medium was conducted. The scan revealed that the RPMI complete medium had two emission peaks, one at 290 nm and the other at 555 nm. It is clear that neither of these peaks would interfere with the peak at 415 nm.

Figure 17:
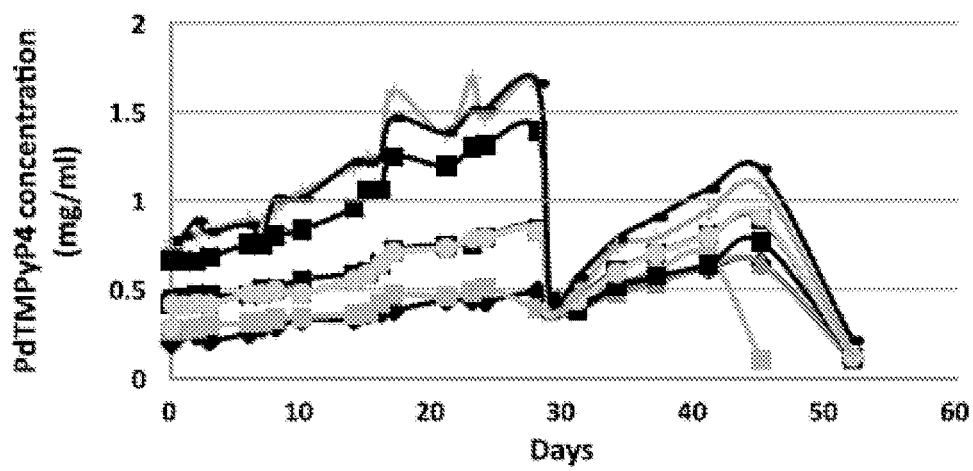
FIG. 17. In vitro release of PdTMPyP4 over 52 days in normal saline.
Figure 18:
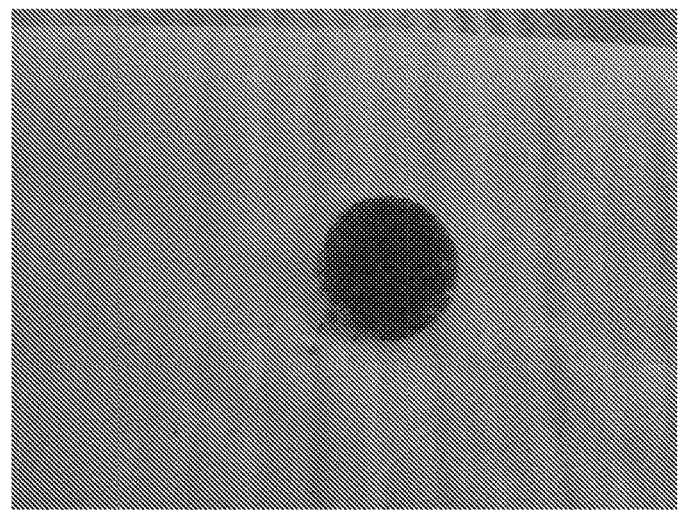
FIG. 18. The device of the invention in the form of a disc is exemplified.
Figure 19:
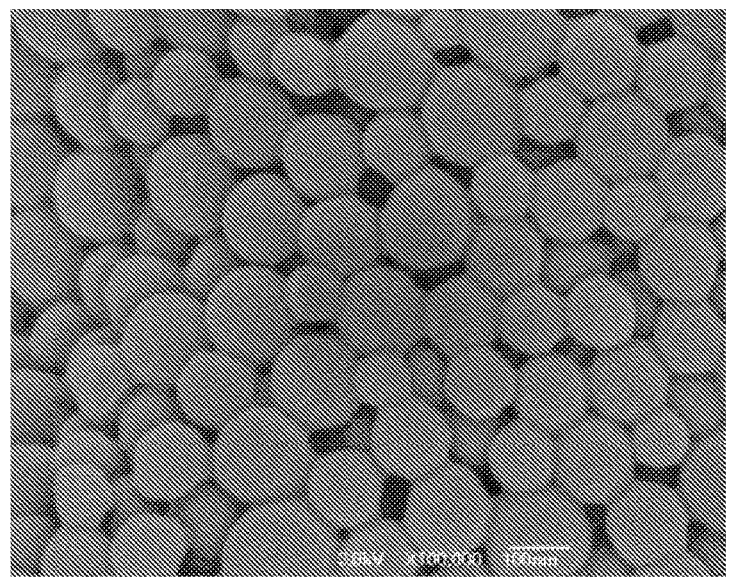
FIG. 19. The device of the invention in the form of nanoparticles is exemplified.
Figure 20:
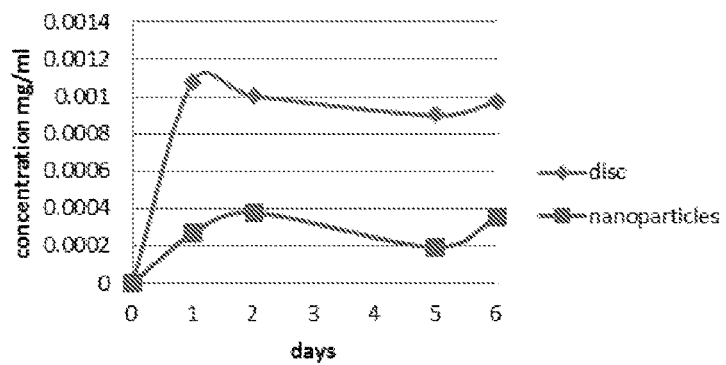
FIG. 20. The in vitro release from the devices in form of disc and nanoparticles is exemplified.

Example 10C—In Vitro Release of PdTMPyP4 from PLGA Rods Over Time in Saline Medium Eight rods, two each of matching weights, were placed in individual Eppendorf tubes with 1 ml of normal saline and incubated at 37° C. For measuring PdTMPyP4 release via absorbance, a 10 µl sample were removed and diluted 1:100 with DDW, and absorbance of the resulting solution measured in the spectrophotometer at 415 nm for the first 28 days. By day 28, when PdTMPyP4 accumulation in the saline neared the maximum detection level of the Optizen instrument, each rod was removed and placed in a new tube with fresh saline. The removal of a 10 µl sample from the fresh saline solution required a 1:10 dilution in DDW for appropriate reading. By day 45, the rods were too fragile to remove from the tube, so the solution was removed and replaced with 1 ml of normal saline and incubated, and an appropriate measurement required a 1:1 dilution. To compare the release of PdTMPyP4 after the various dilutions, the concentrations were normalized to the dilution factor used during the first 28 days (1:100). Typical cumulative release of PdTMPyP4 into normal saline from rods of matched weights over a period of 52 days is shown in FIG. 17.

The polymeric implants, 880-2750 μg in mass, released PdTMPyP4 linearly with time. The curve is divided into two distinct phases. The first phase shows the daily accumulation of PdTMPyP4 from the DDS within the initial 28 days until the sample reached the maximal detection levels of the Optizen spectrophotometer and necessitated the placement of the rods in fresh saline to continue reading PdTMPyP4 absorbance levels. The second phase begins in the fresh saline where there had been no prior accumulation of PdTMPyP4; consequently, a reduction in concentration is observed. However, as PdTMPyP4 is released from the rods and accumulates in the new saline, an increase in the PdTMPyP4 concentration is seen that continues until the disintegration of the rod, somewhere between day 48 and day 52. The cumulative release in both phases of the curve was linear as confirmed by a high R2 of 0.9600. It also appears that the concentration of PdTMPyP4 released from the rods is directly proportional to the mass of the rods. The greater the mass of the rod, the higher the PdTMPyP4 concentration released. All rods, regardless of size, cease from releasing PdTMPyP4 at approximately the same time. Thus, the duration of the release is associated with the period of degradation of the rods, with no correlation to their mass.

Example 10D—In Vitro Release of PdTMPyP4 from PLGA Rods Over Time in Gelatin Gel Several devices with incorporated PdTMPyP4 were prepared and weighed before anchoring them to the base of a cuvette by applying a gelatin layer to the base and awaiting its solidification before filling the cuvette with gelatin. The composition of the gelatin base is similar to the gelatin coating. The gelatin coating is used to measure its impact on drug release or on the duration of the polymer, whereas the gelatin base is used to measure the diffusion of the drug.

The cuvettes were tightly covered with Parafilm® and incubated in a humidified atmosphere with 95% $O_2$, 5% $CO_2$ at 37° C.

As shown herein, the gradual release of the porphyrin under these conditions were attempted in order to decide whether the humidified environment would better the uptake into the tumor. After the first 30 days of this measurement, when the absorption spectra reached its maximum value, the devices were removed, placed in saline and measurement until such time as they degraded condition. Results confirm the long term release of PdTMPyP4 from the device and the gelatin base was considered more reflective of the tumor environment than the saline.

Optical density was measured almost daily for 52 days. Results of the PdTMPyP4 release from the devices are shown in FIG. 12. The legend includes the weight of the rods.

Example 10E—Calculations of PdTMPyP4 Concentration

Figure 2:
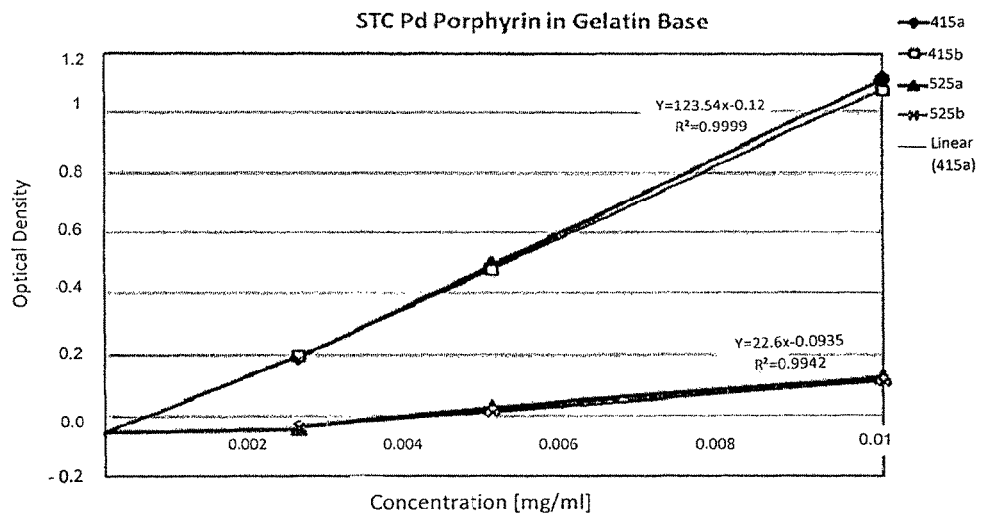
FIG. 2. Standard curve showing PdTMPyP4 absorbance as a function of concentration as measured in a gelatin base.

The standard curves measuring the optical density of the titrated samples of PTMPyP4 in either a gelatin base or DDW are shown in FIGS. 1 and 2. The two peaks that emanated from scanning PdTMPyP4 in DDW are shown in FIG. 1. The peak at 415 nm demonstrated greater absorbance than that at 525 nm and was considered more useful for detecting lower concentrations of the drug. Linear regression analysis yielded a high $R^2$ value of 0.9999 and an equation that could be used to calculate the concentration of an unknown PdTMPyP4 solution based upon its optical density, y=123.54x−0.12. The optical density of PdTMPyP4 was somewhat lower when measured in the gelatin base (FIG. 2) compared to DDW (FIG. 1).

Example 10F—Evaluation of Release from the Implant Devices

To evaluate the release from the implant devices in form of a disk and as nanoparticulate matter, the devices were placed in normal saline and the concentrations of PdTMPyP4 were followed.

For the particles—about 2 mg of nanoparticulate powder, prepared according to the Example 2, accurately weighed, were mixed with 3 ml of normal saline in a 60 mm×15 mm Petri dish.

For the disc—the disc, prepared according to the Example 3, was placed into a 60 mm×15 mm Petri dish and mixed with 5 ml of normal saline.

Aliquots of 10 μl of the solution were withdrawn at specific time points, diluted with 990 μl of normal saline in cuvettes and periodically measured using a spectrophotometer at wavelength of 415 nm. The samples (10 μl) were replaced with fresh normal saline. Both dishes are kept in the incubator at temperature at 37° C.

Example 11—Controlled Release

To further control the release of the hydrophilic PdTMPyP4 in the aqueous medium or tumor environment, a gel solution for coating the rods was prepared. The gel consists of 10 g gelatin, 35 ml glycerol and 9 ml of DDW. The individual rods are dipped into the liquid heated gel to coat the devices and the gel is given time to solidify upon cooling. Although only a single layer was applied to the devices used in these experiments, the application of multiple layers is feasible. In cases where one might prefer to delay the output of the devices, this approach can be considered.

Example 12—Effect of Coating Rods with Gelatin on PdTMPyP4 Release

To observe the effect of the gelatin coating on the release of PdTMPyP4, 4 devices containing PdTMPyP4 were prepared. Two of these were coated with a layer of gelatin and 2 were left uncoated.

Each device was placed in the base of a 1.5 ml Eppendorf tube containing 1 ml of complete RPMI medium. The uncapped tubes were incubated at 37° C. and 5% $CO_2$ prior to spectrophotometry at a wavelength of 415 nm. The release of PdTMPyP4 was very rapid and the color so intense that all samples had to undergo a 1:10 dilution. Double distilled water (DDW) was used for the dilutions to represent the aqueous tumor environment. PdTMPyP4 release was measured spectrophotometrically at 2, 24, and 48 h. Results are shown in the FIG. 3.

Figure 3:
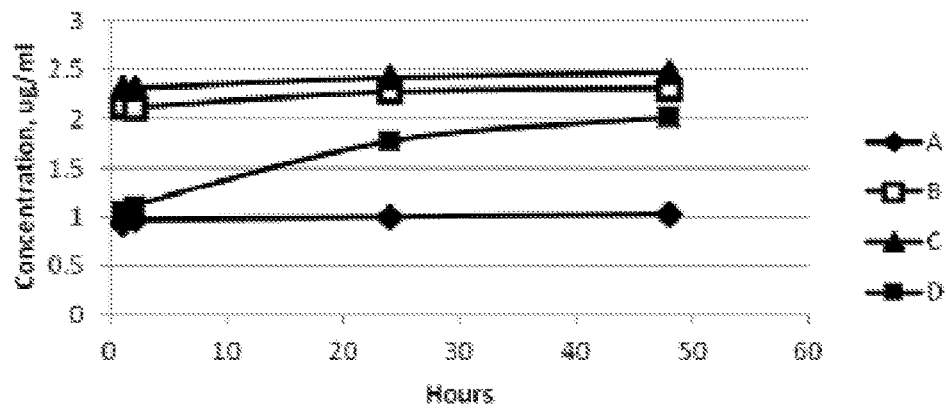
FIG. 3. PdTMPyP4/PLGA rods A and D, weighing 0.00126 g and 0.00060 g, respectively, were coated with one layer of gelatin. Rods B and C, weighing 0.00112 and 0.00096 g, respectively, remained uncoated.

The equation shown in FIG. 1 was used to calculate the PdTMPyP4 concentration over this 48-h period. All samples required dilution to remain within the detection level of the spectrophotometer and the dilution factor was included in the calculation. FIG. 3 show that the PdTMPyP4 release from the gel-coated device A is relatively stable throughout; however, release from gel-coated device D increases over time and appears to approach the release in samples B and C. Without being bound by a specific theory, this phenomenon may reflect damage to the gelatin coating when the devices were removed from the solution with forceps in order to perform the spectroscopy. The weights of the devices apparently had no effect on PdTMPyP4 release. Device A and Device B were of similar weights as were Devices C and D. Thus the difference in release appears to be related to the gel coating. Both of these parameters would ultimately affect the duration of time that porphyrin is in the tumor because of the biodegradability of the device. It also remains unclear whether the gel coating slows the diffusion of the porphyrin or whether it slows the biodegradation of the polymer. Nevertheless, it is apparent from the studies shown below that a decrease in L428 cell survival required a much longer exposure of the cells to the PdTMPyP4 inhibitor. This is likely due to the lag time between telomerase inhibition and telomere shortening.

As demonstrated above, the experiments described herein demonstrated the biological efficacy of the continuous, long-term controlled release of a telomerase-inhibiting drug, PdTMPyP4, that affords a gradual and continuous release rate for >30 days beneficial as adjuvant to radio-therapeutic or chemotherapeutic procedures, because it does not interfere with those treatment procedures or as an independent treatment modality, described herein.

The biodegradable drug delivery device that was developed and used here sustained a relatively stable release of PdTMPyP4 throughout the 19-day experiment. Although the exponential growth of the model L428 cancer cells was constantly encouraged, as described in further detail below, it could not be sustained in those cells continuously exposed to PdTMPyP4 compared to untreated control cells and those incubated with a blank device.

It may be difficult to maintain the continuous presence of a telomerase inhibitor in tumors, particularly if it is a hydrophilic molecule. The PdTMPyP4/PLGA device disclosed and exemplified herein provides the advantage of direct intratumoral implantation and the release of a well-studied porphyrin whose mechanisms of action have been defined.

Further, by avoiding systemic drug administration and focusing on direct intratumoral drug release, the present invention avoids problems associated with the rapid clearance of the drug from tumor and the effect of the drug on normal tissues. Herein also demonstrated success in the manufacturing and release of PdTMPyP4 from PLGA devices in in vitro and in vivo studies. The results in FIG. 15 suggest continuity in the release of PdTMPyP4 within the specific tumor environment.

Figure 16:
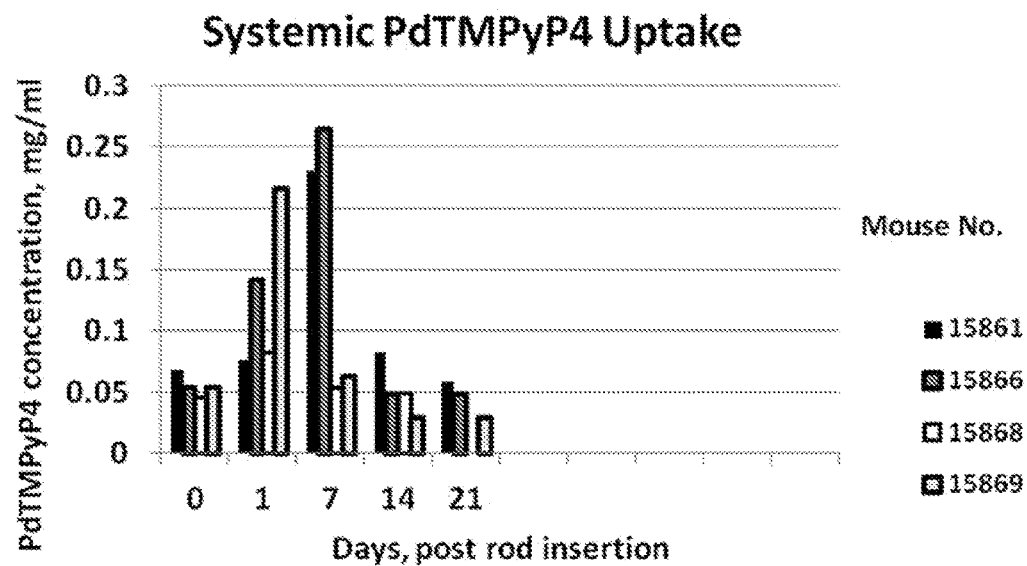
FIG. 16. Weekly measurements of PdTMPyP4 concentration in blood plasma of 4 BALB/c mice with 1 PdTMPyP4/PLGA rod inserted into each tumor.

Its negligible uptake in the systemic circulation, as shown in the FIG. 16 indicates that it remains largely within the tumor, thereby maximizing intra-tumoral drug loading thus continuously sustaining the inhibition and prevent telomerase reactivation and telomere re-lengthening.

The devices of the present invention are implanted directly into the tumor and enter the systemic circulation in minimal amounts and, as shown in FIG. 16, for a very brief period of time. Accordingly, normal tissues are minimally adversely affected.

The results of the ex vivo study in FIG. 15 and the in vivo study in FIG. 13 show that the devices of the present invention provide an effective intratumoral drug concentration over the long term.

The concentration of the drug that is released is proportional to the mass of the implant, as demonstrated in FIG. 17 and that the duration of the release is related to the rate of degradation of the polymer and unrelated to its mass. Therefore, optimizing the drug delivery profile for clinical use would involve alterations in the size or mass of the polymeric implants to personalize the treatment for effective dosage delivery, or, if necessary, serial intra-tumoral implants to assure the continuous presence of the drug in tumor should >30 days be required. Due to multiparticulate nature of the devices of the present invention, such optimization is made readily available to clinicians.

The procedure for preparing the implant is amenable to structural alterations. In addition, another aspect of the versatility of the intra-tumoral DDS implant of the present invention lies in its flexibility to support a personalized treatment program that will accommodate and be responsive to the status of a patient's tumor. For example, telomerase activation and telomere length are measurable and quantifiable upon biopsy and, together with diagnostic imaging, can provide an assessment of the extent to which the implant is effective.

The therapeutic gain from Auger emission can also compensate for the decaying radioactivity of the seeds (T½ iodine-125=about 60 days) over time, enhance the radiation dose delivered to the tumor and prevent telomere elongation.

In fact, this same principle would apply to the promoter region of the c-myc oncogene where TMPyP4 also binds to the GQ in the promoter region of the c-myc oncogene.

Fragmenting the c-myc loci may also contribute to DNA damage and to a reduction in telomerase activity by reducing hTERT activation (Grand et al., 2002, Mol Cancer Ther 1:565-573).

In summary, described herein is the development of an intratumoral polymeric implanted devices that continuously releases a telomerase-inhibiting drug over the long term after a single application. Long-term, continuous telomerase inhibition prevents the immortalization of those cancer cells surviving the initial steps of conventional cancer treatments and increases the sensitivity of the cancer cell to subsequent therapeutic procedures. A more comprehensive treatment for anatomically accessible tumors is also proposed. The intratumoral insertion of the PdTMPyP4 devices and/or the photo-activation of co-localized with the DNA palladium atoms by photons from brachytherapy, for example, iodine-125 seeds or synchrotron radiation beams may result in a powerful combination that severely damages cancer cell DNA via the Auger effect, inhibits the activation of telomerase and induces cancer cell lethality by shortening telomeres elongated by ALT (Laster et al. 2009). All of these events pertain to the use of a single molecule whose individual components (heavy metal and TMPyP4) independently counteract the cancer cell's activation of survival mechanisms that prevent the shortening of telomeres and can lead to their immortalization.

The invention claimed is:

1. A solid implant device suitable for the long-term, controlled release of a telomerase-inhibiting agent comprising Pd-meso-tetra(N-methyl-4-pyridyl)-porphyrin into tumor tissue, wherein said device comprises a homogeneous solid mixture of the Pd-meso-tetra(N-methyl-4-pyridyl)-porphyrin and poly-(lactic-co-glycolic) acid copolymer formulated for a long term controlled release of greater than 19 days of said Pd-meso-tetra(N-methyl-4-pyridyl)-porphyrin, wherein said implant device is in the form of a solid body that is implantable directly into tumor tissue, and wherein the solid mixture has a degree of homogeneity that can be obtained by solidifying a homogeneous solution of the Pd-meso-tetra(N-methyl-4-pyridyl)-porphyrin and the poly-(lactic-co-glycolic) acid copolymer.

2. The device according to claim 1, wherein the telomerase-inhibiting agent loading is from 0.001% w/w to 70% w/w.

3. The device according to the claim 2, wherein the telomerase-inhibiting agent loading is between 1% and 50% w/w.

4. The device according to claim 1, wherein said solid implant device is in the form of a solid rod-like body.

5. The device according to claim 1, wherein said implant is obtained by solidifying a homogeneous solution of Pd-meso-tetra(N-methyl-4-pyridyl)-porphyrin and poly-(lactic-co-glycolic) acid copolymer.

6. A method of treatment of cancer with controlled delivery of a telomerase-inhibiting agent comprising Pd-meso-tetra(N-methyl-4-pyridyl)-porphyrin into a tumor, comprising:
implanting directly into a tumor an implant device in accordance with claim 1, thereby treating the cancer, with the proviso that the treatment occurs without the concurrent placement of brachytherapy seeds in or at the vicinity of the tumor.

7. The method of claim 6, wherein the implant device is in the form of a solid rod-like body.

8. A method of treatment of cancer, comprising:
implanting directly into a tumor an implant device in accordance with claim 1; and
simultaneously placing brachytherapy seeds in or at the vicinity of the tumor.

9. The method of claim 8, wherein the implant device is in the form of a solid rod-like body.

10. A method of treatment of cancer in a patient in need thereof, comprising intratumorally administering to said patient at least one device according to claim 1.

11. The method according to the claim 10, further comprising concomitant administration to said patient at least one brachytherapy seed in or at the vicinity of the tumor.

* * * * *